(12) United States Patent
Van Der Schaaf et al.

(10) Patent No.: US 7,442,838 B2
(45) Date of Patent: *Oct. 28, 2008

(54) POLYMORPHIC FORMS OF SERTRALINE HYDROCHLORIDE

(75) Inventors: Paul Adriaan Van Der Schaaf, Hagenthal-le-Haut (FR); Franz Schwarzenbach, Frenkendorf (CH); Hans Jürg Kirner, Pratteln (CH); Martin Szelagiewicz, Münchenstein (CH); Claudia Marcolli, Zürich (CH); Andreas Burkhard, Basel (CH)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 83 days.

This patent is subject to a terminal disclaimer.

(21) Appl. No.: 11/101,860

(22) Filed: Apr. 8, 2005

(65) Prior Publication Data

US 2005/0197404 A1 Sep. 8, 2005

Related U.S. Application Data

(63) Continuation-in-part of application No. 10/736,195, filed on Dec. 15, 2003, now Pat. No. 6,939,992, which is a continuation of application No. 10/111,947, filed as application No. PCT/EP00/10416 on Oct. 23, 2000, now Pat. No. 6,872,853.

(30) Foreign Application Priority Data

Oct. 29, 1999 (EP) ................... 99810981

(51) Int. Cl.
*C07C 211/42* (2006.01)

(52) U.S. Cl. .................................... 564/308

(58) Field of Classification Search ............... 564/308, 564/428
See application file for complete search history.

(56) References Cited

U.S. PATENT DOCUMENTS

| | | | |
|---|---|---|---|
| 4,536,518 A | 8/1985 | Welch, Jr. et al. | 514/647 |
| 5,082,970 A | 1/1992 | Braish | 564/424 |
| 5,248,699 A | 9/1993 | Sysko et al. | 514/647 |
| 5,463,126 A | 10/1995 | Williams | 564/222 |
| 5,734,083 A | 3/1998 | Wilson et al. | 564/308 |
| 6,495,721 B1 | 12/2002 | Schwartz et al. | 564/308 |
| 6,939,992 B2 * | 9/2005 | Van Der Schaaf et al. | 564/308 |

FOREIGN PATENT DOCUMENTS

| | | |
|---|---|---|
| EP | 0928784 | 7/1999 |
| JP | 2000-26378 | 1/2000 |
| WO | 98/27050 | 6/1998 |
| WO | 99/47486 | 9/1999 |
| WO | 00/32551 | 6/2000 |
| WO | 03/093217 | 11/2003 |

OTHER PUBLICATIONS

Prof. Dr. Jürgen Falbe et al., Römpp Chemie Lexikon, 10. Ed., p. 1896 (1979).
Wolfgang Beckmann et al., Organic Process Research & Development, vol. 2, No. 5, pp. 298-304 (1998).
J. B. Conant et al., Organic Syntheses, CV 1, 345.
L. G. Wade, Organic Chemistry, $2^{nd}$ Ed., pp. 998-1001, (1991).

* cited by examiner

*Primary Examiner*—Samuel A Barts
(74) *Attorney, Agent, or Firm*—Mervin G. Wood

(57) ABSTRACT

Sertraline hydrochloride polymorphic form II is conveniently prepared by adding hydrogen chloride to solution of sertraline free amine in a ketone. In preferred processes, the solution of sertraline free amine seeded with some crystals of polymorphic form II and/or the solution is heated before addition of the hydrogen chloride.

9 Claims, 4 Drawing Sheets

POLYMORPHIC FORMS OF SERTRALINE HYDROCHLORIDE

This is a continuation-in-part of application Ser. No. 10/736,195, now U.S. Pat. No. 6,939,992, filed Dec. 15, 2003, which is a continuation of application Ser. No. 10/111,947, now U.S. Pat. No. 6,872,853, filed Apr. 26, 2002, which is the National Stage of International Application No. PCT/EP 00/10416, filed Oct. 23, 2000.

The present invention relates to an improved process for the preparation of crystalline polymorphic form II of (1S-cis)-4-(3,4-dichlorophenyl)-1,2,3,4-tetrahydro-N-methyl-1-naphthalenamine hydrochloride, i.e. sertraline hydrochloride.

Sertraline hydrochloride is useful as an antidepressant and anorectic agent, and is also useful in the treatment of chemical dependencies, anxiety-related disorders and premature ejaculation, and is described in U.S. Pat. No. 4,536,518 (Pfizer Inc.). Sertraline hydrochloride can exist in different crystalline forms, polymorphic forms, which differ from each other in their stability, physical properties, spectral data and methods of preparation. Sertraline has the following structural chemical formula:

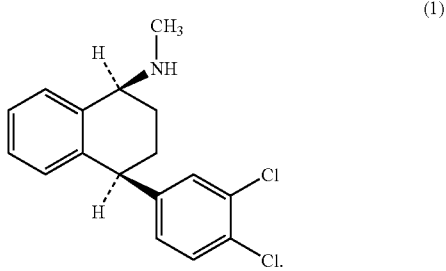

U.S. Pat. No. 4,536,518 (Pfizer Inc.) discloses the synthesis of sertraline hydrochloride. The amine is dissolved in a mixture of diethyl ether and ethyl acetate and reacted with hydrogen chloride gas. The reference states that the compounds of this invention may exist in different polymorphic forms, i.e. different crystalline forms. The reference does not refer to specific polymorphic crystalline forms of sertraline hydrochloride. U.S. Pat. No. 5,248,699 (Pfizer Inc.) discloses 5 polymorphic forms of sertraline hydrochloride (I, II, III, IV, and V) as well as methods for preparing them. The reference further discloses that 'the synthetic procedure described and exemplified in U.S. Pat. No. 4,536,518 produces the sertraline hydrochloride polymorph designated herein as Form II'. U.S. Pat. No. 5,734,083 (Torcan Chemical Ltd.) discloses a further polymorphic form of sertraline hydrochloride (=T1), together with the process of preparation.

Although it is disclosed in U.S. Pat. No. 5,248,699 (Pfizer Inc.) that polymorphic form I exhibits the greatest stability of the crystalline forms of sertraline hydrochloride, the solubility of this form may be insufficient for successful application. For example, the rate of absorption of a drug is dependent upon the dissolution rate. The dissolution rate and the rate of absorption will either increase or decrease depending upon the polymorph present. The most stable polymorph will have the lowest solubility and in many cases the slowest dissolution rate. Other less stable polymorphs will usually have higher dissolution rates. [Stephen R. Byrn in "Solid-State Chemistry of Drugs", Academic Press, New York, 1982].

Several attempts have been made to improve the process for producing the metastable polymorphic form II of sertraline HCl (see, for example, JP-A-2000-26378; U.S. Pat. No. 6495721). The reliability of the known processes and the purity of the product, in terms of crystal form as well as chemical purity, still require improvement.

Sertraline hydrochloride polymorphic form II may be formed from a solution of sertraline free amine with some seeding crystals of form II I before or after the addition of hydrogen chloride, e.g. as a solution of hydrogen chloride; or from a stirred suspension of sertraline hydrochloride polymorphic form V with some seeding crystals of sertraline hydrochloride polymorphic form II; or by drying a sertraline hydrochloride alcohol solvate at temperatures from about 0 to 30° C. in high vacuum (<1 mbar); or from stirred suspensions of certain other polymorphic form of sertraline hydrochloride with some seeding crystals of sertraline hydrochloride polymorphic form II. Sertraline hydrochloride polymorphic form II may further be formed according to a process, wherein a solution of sertraline free amine is seeded with some crystals of polymorphic form II and hydrogen chloride is added (see appl. U.S. Ser. No. 10/111,947; WO01 032601).

It has been found that Sertraline hydrochloride polymorphic form II is preferentially formed from a ketone solution. Thus, present invention pertains to a process, wherein hydrogen chloride is added to a solution of sertraline free amine in a ketone. In a preferred process, the solution is seeded with some crystals of polymorphic form II.

The hydrogen chloride used can be added, for example, as a solution in an organic solvent, like a ketone as given above, as an aqueous solution, or as hydrogen chloride gas. In a preferred process, hydrogen chloride is added until a pH less than 5.5, especially less than 5, is reached.

It is preferred to add the seeding crystals of polymorphic form II before addition of the solution of hydrogen chloride. Typical amounts of seeding crystals are 0.1 to 10 mol-%, based on the molar amount of sertraline.

In the presently preferred process for the preparation of sertraline hydrochloride polymorphic form II, hydrogen chloride is added after heating the solution.

The starting solution in this case is a clear solution not containing any visible traces of crystals of sertraline or sertraline hydrochloride impurities. If desired, the solution may be subjected to an additional filtration step before or after heating. Before addition of hydrogen chloride and, optionally, the seeding crystals, the concentration of any form of sertraline dissolved is well below saturation, for example below 80%, preferably below 50% of the saturated solution. For example, ketone solutions containing about 5 to about 20% by weight of sertraline free amine can be used. Any impurity of sertraline hydrochloride at this stage should be avoided; preferably it is, if present, kept below 1% by weight.

In a preferred process, the solution is heated to 45-80° C. prior to addition of hydrogen chloride.

Preferred are ketone solvents of formula $R_1$—CO—$R_2$, wherein $R_1$ and $R_2$ are $C_1$-$C_4$alkyl, especially where $R_1$ is $C_1$-$C_4$alkyl and $R_2$ is $C_2$-$C_4$alkyl. Examples for $R_1$ and $R_2$ are methyl, ethyl, n- or i-propyl and n-, s-, i- or t-butyl.

$R_1$ is preferably methyl. $R_2$ is preferably methyl, ethyl or butyl such as isobutyl. Examples of ketones are acetone, methyl ethyl ketone, methyl propyl ketone, methyl butyl ketone, methyl isobutyl ketone. In a preferred process, a solution of sertraline free amine in a water-immiscible ketone is used.

The process is usually carried out with the ketone as the sole solvent, any other solvent, including the one for adding hydrogen chloride, preferably being kept at a level below 20% of the total amount of solvent used. Of special technical interest is a process wherein essentially no other solvent than a ketone is used (and thus present during crystallization).

It is preferred to add seeding crystals of polymorphic form II before addition of hydrogen chloride. In certain cases, especially if a solution of low concentration is used, however, the order of addition may also be reversed, i.e. hydrogen chloride is added to the solution of sertraline free amine and subsequently the solution is seeded with some crystals of polymorphic form II.

Typical amounts of seeding crystals are 0.1 to 10 mol-%, preferably 1 to 10, especially 2 to 10 mol-%, based on the molar amount of sertraline.

Seeding crystals and HCI or hydrochloric acid usually is mixed with the solution by a separate measure such as stirring.

Workup and isolation of the product, including drying, may be effected using methods known in the art. In a preferred process, sertraline hydrochloride form II is separated from the liquid phase, washed with a pharmaceutically acceptable solvent and dried. Sertaline free base and its solution in a ketone used in present process may be prepared in situ; thus, present invention further pertains to a process, wherein a solution of sertraline free amine is obtained from sertraline mandelate. In a preferred process, the solution of sertraline free amine is obtained after a) treating a solution of sertraline mandelate in a ketone immiscible with water, with an aqueous hydroxide,
b) phase separation and
c) washing the ketone solution with water.

This invention also relates to a pharmaceutical composition comprising polymorphic form II as obtained in the present process effective in treating depressions, anxiety-related disorders, obesity, chemical dependencies, or addictions or premature ejaculations in a human, and a pharmaceutically acceptable carrier.

The present polymorphic form may be used as single components or mixtures.

The following examples will illustrate, but do not limit the scope of the present invention. Whereever used, room temperature denotes a temperature in the range 20-30° C. Percentages are given by weight, unless otherwise specified.

EXAMPLE 1

Preparation of Polymorphic Form II in Acetone Without Heating 24 g sertraline free amine are dissolved in 280 ml acetone. To this solution 1.2 g sertraline hydrochloride polymorphic form II are added as seeding crystals. To this mixture are added dropwise 53.7 g of a solution of HCl in acetone (5.33 wt %) at room temperature. The resulting white suspension is stirred for an additional 2 h, filtered, and the resulting white product washed with acetone (2×20 ml). The product is dried in vacuum (0.1 mbar) for 16 h.

The product is obtained in 91% isolated yield.

Raman and X-ray powder diffraction studies show the product to be polymorphic form II (see FIGS. 3 and 4).

EXAMPLE 2

Preparation of Polymorphic Form II in Acetone using Aqueous HCl with Heating 50 g of sertraline free amine are dissolved in 500 ml acetone. This solution is clarified by filtration, and the clear solution is well stirred and heated to reflux temperature. At this temperature 2.5 g (5 mol %) of sertraline hydrochloride Form II are added after which directly the addition of the aqueous hydrogenchloride solution (32%) is started until pH<5. The resulting white suspension is cooled to −5°C. and sertraline hydrochloride is isolated by filtration and dried in vacuum. The sertraline is obtained as Form II.

EXAMPLE 3

Preparation of Polymorphic Form II using Methyl Ethyl Ketone and Ag. HCI 10 g sertraline free amine are dissolved in 85 ml methyl ethyl ketone. This solution is clarified by filtration, and the clear solution is well stirred and heated to 60° C. At this temperature 0.5 g (5 mol %) of sertraline hydrochloride Form II are added after which directly the addition of the aqueous hydrogenchloride solution (37%) is started until pH<5. The resulting white suspension is cooled to −5° C. and sertraline hydrochloride is isolated by filtration and dried in vacuum. The sertraline is obtained as Form II.

EXAMPLE 4

Preparation of Polymorphic Form II using Methyl Isobutyl Ketone and Ag. HCI 40 g sertraline free amine are dissolved in 360 ml methyl isobutyl ketone. This solution is clarified by filtration, and the clear solution is well stirred and heated to 60° C. At this temperature 2 g (5 mol %) of sertraline hydrochloride Form II are added after which directly the addition of the aqueous hydrogenchloride solution (37%) is started until pH<5. The resulting white suspension is cooled to 20° C. and sertraline hydrochloride is isolated by filtration and dried in vacuum. The sertraline is obtained as Form II.

EXAMPLE 5

Preparation of Polymorphic Form II using Methyl Isobutyl Ketone and HCl Gas 129.6 kg of enantiopure sertraline mandelate are dissolved in methyl isobutyl ketone. Sodium hydroxide (50% aqueous solution) is added to convert the mandelate into sertraline free base. The organic phase is separated, washed with water, and dried by azeotropic distillation. The organic phase is cooled to room temperature, filtered, and subsequently heated to 55-60° C. Seeding crystals of sertraline HCl form II (4.8 kg) are added, and subsequently HCl gas is bubbled into the liquid until pH 4 is reached, while the mixture is constantly stirred. The mixture is cooled in 2 steps to 40-45° C. and then to 15-20° C., where the solid product is filtered off, washed with methyl isobutyl ketone and subsequently with isopropyl acetate, and then dried at 30° C. 100.4 kg of pure sertraline form II hydrochloride (97.2% relative to mandelate educt) are obtained (identified by X-ray powder diffraction, pattern as in FIG. 3).

Figure 1:
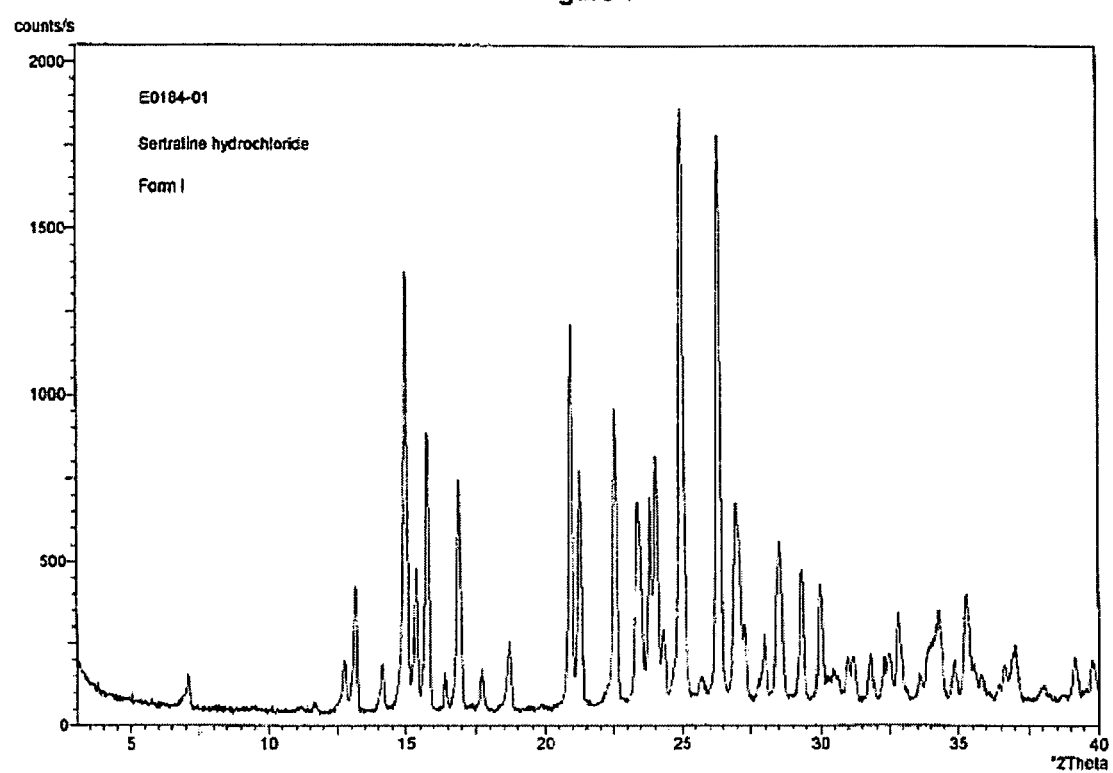
FIG. 1 is a characteristic X-ray powder diffraction pattern for polymorphic form I
Figure 2:
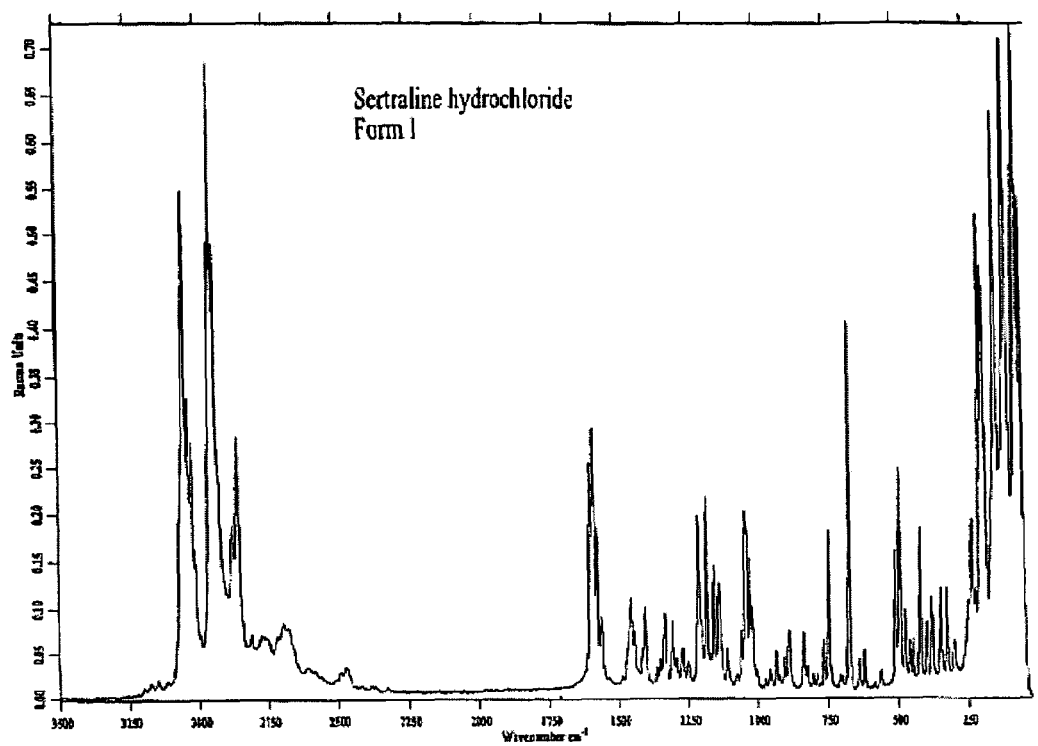
FIG. 2 is a characteristic Raman spectrum of polymorphic form I
Figure 3:
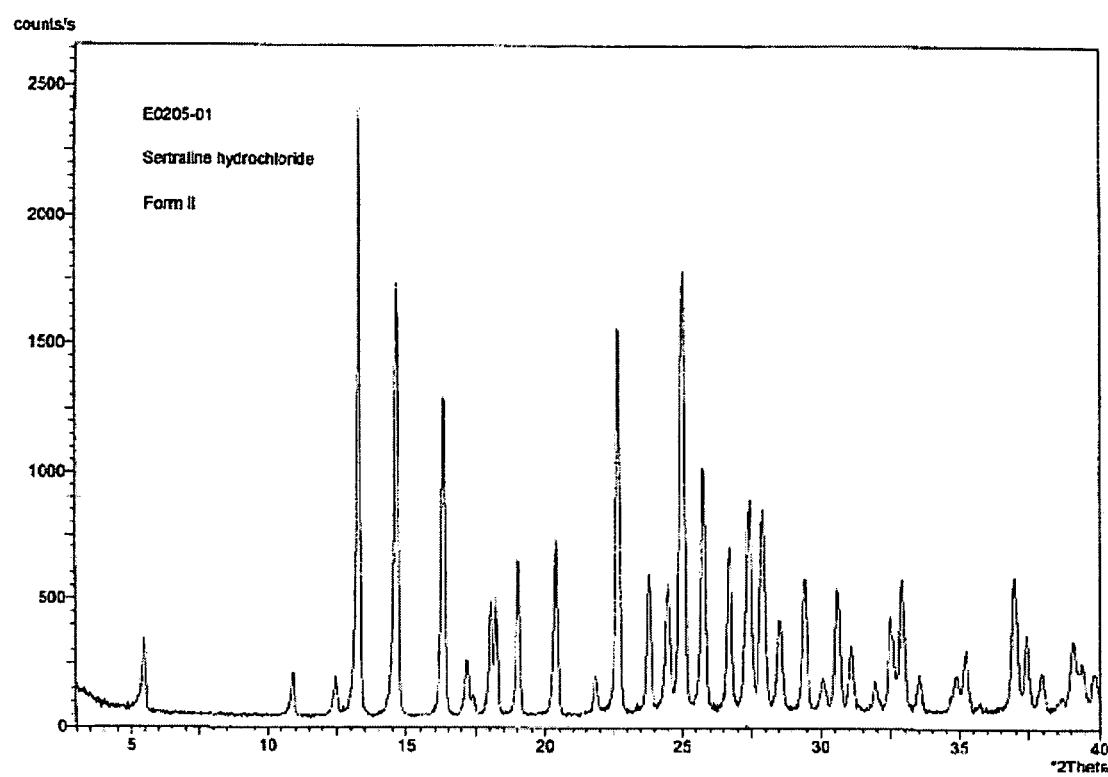
FIG. 3 is a characteristic X-ray powder diffraction pattern for polymorphic form II
Figure 4:
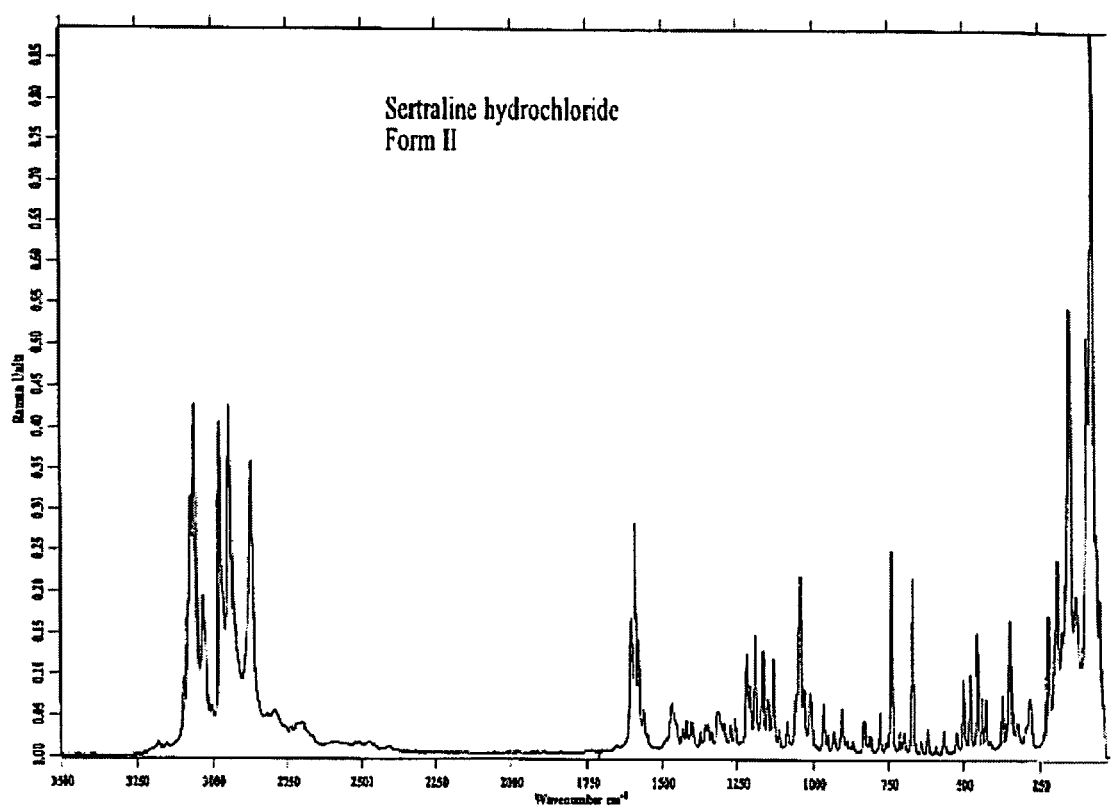
FIG. 4 is a characteristic Raman spectrum of polymorphic form II

The invention claimed is:

1. A process for the preparation of sertraline hydrochloride polymorphic form II, wherein hydrogen chloride is added to a solution of sertraline free amine in a ketone selected from the group consisting of acetone, methyl ethyl ketone, and methyl isobutyl ketone wherein sertraline hydrochloride polymorphic form II is crystallized out of said solution.

2. A process according to claim 1, wherein the solution of sertraline free amine is seeded with some crystals of polymorphic form II.

3. A process according to claim 2 wherein the solution of sertraline free amine is seeded with some crystals of polymorphic form II and subsequently hydrogen chloride is added.

4. A process according to claim 2 wherein hydrogen chloride is added to the solution of sertraline free amine and subsequently the solution is seeded with some crystals of polymorphic form II.

5. A process according to claim 1 wherein hydrogen chloride is added as a solution.

6. A process according to claim 5, wherein hydrogen chloride is added as an aqueous solution.

7. A process according to claim 2, wherein the amount of seeding crystals used is 0.1 to 10 mol-%, based on the molar amount of sertraline.

8. A process according to claim 1, wherein the solution is heated before addition of the hydrogen chloride.

9. A process according to claim 2, wherein the solution is heated before addition of the hydrogen chloride.

* * * * *